United States Patent [19]

Mangel et al.

[11] Patent Number: 4,557,862
[45] Date of Patent: Dec. 10, 1985

[54] RHODAMINE DERIVATIVES AS FLUOROGENIC SUBSTRATES FOR PROTEINASES

[75] Inventors: Walter F. Mangel, Urbana, Ill.; Stephen Leytus, Seattle, Wash.; L. Lee Melhado, Urbana, Ill.

[73] Assignee: University Patents, Inc., Westport, Conn.

[21] Appl. No.: 546,718

[22] Filed: Oct. 28, 1983

[51] Int. Cl.$^4$ ........................ C07G 7/00; C07D 493/10
[52] U.S. Cl. ........................ 260/112 R; 260/112.5 R; 549/227; 436/800; 435/4; 435/23; 435/219; 435/184; 435/188; 252/301.16
[58] Field of Search ................ 260/112 R, 112.5 R; 549/227; 436/800

[56] References Cited

U.S. PATENT DOCUMENTS 4,433,156 2/1984 Ishige et al. .......................... 549/227
4,436,926 3/1984 Sato et al. ............................ 549/227

FOREIGN PATENT DOCUMENTS 1155551 10/1963 Fed. Rep. of Germany .
6121039 9/1981 Japan .

OTHER PUBLICATIONS

Chem. Abstract No. 208604b, Rhodamine-Based Compds. . . . Proteinases, Leytus et al., vol. 99, 1983.
Chem. Abstract No. 2653x, New Class of Sensitive and Selective . . . Derivatives of Rhodamine, Leytus vol. 100, 1984.

*Primary Examiner*—John Kight
*Assistant Examiner*—Garnette D. Draper
*Attorney, Agent, or Firm*—George M. Yahwak

[57] ABSTRACT

The present invention relates to a new class of novel Rhodamine derivatives. These derivatives which are bisamide substitution products are nonfluorescent. Whereas the monoamide substitution products exhibit high fluorescence. Cleavage of a single specified amide bond by bond-specific proteinases will therefore convert the nonfluorescent bisamide derivative into a highly fluorescent monoamide derivative.

10 Claims, No Drawings

RHODAMINE DERIVATIVES AS FLUOROGENIC SUBSTRATES FOR PROTEINASES

This invention results in part from research conducted under a grant received from the National Institutes of Health.

The present invention relates to a new class of Rhodamine derivatives that are the most sensitive and selective substrates for proteases yet described.

Proteases constitute a large and important group of enzymes involved in such diverse physiological processes as blood coagulation, inflammation, reproduction, fibrinolysis, and the immune response. Numerous disease states are caused by and can be characterized by, the alterations in the activity of specific proteases and their inhibitors; measurement of these alterations are therefore clinically significant in the treatment and management of the underlying disease states. Proteases, however, are not easy to assay—with their natural substrates, the assays are difficult to perform and expensive; with currently available synthetic substrates, the assays are expensive, insensitive, and nonselective. Furthermore, with the use of either the naturally occurring substrate or the presently available synthetic substrates, high concentrations of the target protease are required which results, in part, in the self destruction of the protease.

The new class of Rhodamine derivatives of the present invention have several characteristics that render them useful as protease substrates. For example, they are very soluble and stable in aqueous solutions at neutral pH. These derivatives are also relatively nonfluorescent and have small extinction coefficients, however, cleavage of a single amide bond in the bisamide derivative substrate by an appropriate protease, that is an amidase necessary for cleavage of the amide immediately adjacent to (the "$P_1$" position) the Rhodamine core molecule, results in a monoamide product with a 3500-fold increase in fluorescence intensity and a large extinction coefficient. In addition, these Rhodamine derivatives have other obvious advantages as diagnostic agents for proteases: the derivatives are relatively inexpensive to synthesize and purify to high levels; because they are extremely sensitive substrates, only very small amounts of the biological sample (e.g., blood, urine, etc.) are required to perform the clinical assay for the enzyme; because the derivatives are extremely selective substrates, little or no purification of the biological sample is required; and because all the compounds maximally absorb at 491 nm and emit at 523 nm (where the output from a xenon lamp is relatively high) where interference from most biological materials is low. Since the same wavelengths are used for each substrate, a simple and relatively inexpensive dedicated spectrofluorometer can be designed and built around these wavelengths with which to assay a wide variety of proteases, and because the change in absorbance upon hydrolysis is so great, i.e., 400-fold, these substrates can also be used, at a somewhat reduced sensitivity, in spectrophotometers which are presently available.

Synthetic fluorogenic amide substrates have previously proved to be valuable reagents for the quantitative assay for serine proteases. Of the various primary aromatic amides which have been developed for this purpose, the coumarin derivatives (specifically derivatives of 7-(N-Cbz-L-argininamido)-4-methylcoumarin) have offered the greatest sensitivity and have been the most widely used.

Two important criteria for the selection of a fluorophore for incorporation into a synthetic enzyme substrate are the detectability of the fluorophore and the reactivity of the bond undergoing cleavage. Despite the usefulness of courmarin-based substrates, less than optimal conditions for detection of the fluorophore must be used to maximize the spectral differences between substrate and product. Furthermore, no structural change occurs within the aminocoumarin moiety on cleavage of the substrate that would be expected to make amides formed from aminocoumarins especially reactive.

Rhodamine is a diamino analogue of Fluorescein having the following structure:

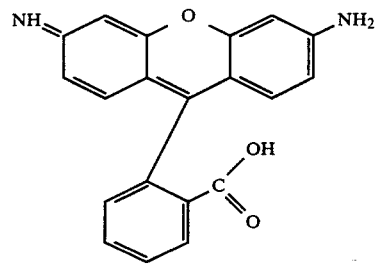

When the amino groups of Rhodamine are blocked by acetylation this intensely coloured dye is converted into a colourless and presumably non-fluorescent form, implying that the conjugation system of the chromophore is interrupted. This ability to be converted into a colourless and presumably non-fluorescent form upon formation of derivatives is a desirable spectral property for a fluorogenic substrate. Thus Rhodamine was believed to be a highly reactive fluorophoric leaving group, since loss of acylation is accompanied by a large increase in the degree of conjugation and hence a large increase in stability. However, amino acid derivatives of Rhodamine were not synthesized prior to the present invention, and therefore the use of the amino acid derivatives of Rhodamine as fluorogenic substrates for the amidase activity of serine proteinases were never available for use as well.

The synthesis of dipeptide derivatives according to the present invention comprises a three step procedure: (1) the synthesis of bis(blocked amino-NH)$_2$-Rhodamine derivative, (2) the synthesis of bis(amino-NH)$_2$-Rhodamine derivative from the step 1 product, and (3) the synthesis of the dipeptide derivative. The synthesis of the dipeptide derivatives can be more easily understood by reference to Examples I, II, and III, (each of which corresponds to steps 1, 2, and 3, respectively) in the synthesis of a specific dipeptide derivative according to the present invention.

In these examples, and throughout this disclosure, the abbreviation "Cbz" refers to the commonly used blocking group benzyloxycarbonyl although other recognized blocking groups (such as t-butyl oxtycarbonyl) may also be used attached to the end position ($P_n$) amino acid or internal amino acids as well; the position of each amino acid is indicated as "$P_{1,2,3...n}$" depending upon the distance removed from the fluorophore core; and the amino acid substitution moieties, which can include any of the known amino acids or amino acid derivatives, are defined in accordance with their accepted abbreviations, that is "Ala" is Alanine, "Arg" is Arginine, "Asn" is Asparagine, "Asp" is Aspartic acid, "Cys" is Cysteine, "Gln" is Glutamine, "Glu" is Glutamic acid, "Gly" is Glycine, "His" is Histidine, "Ile" is Isoleucine, "Leu" is Leucine, "Lys" is Lysine, "Met" is Methionine, "Phe" is Phenylalanine, "Pro" is Proline, "Ser" is Serine, "Thr" is Threonine, "Trp" is Tryptophan, "Tyr" is Tyrosine, "Val" is Valine, "Hcy" is Homocysteine, etc.

EXAMPLE I

SYNTHESIS OF (Cbz—Arg—NH)$_2$-RHODAMINE

To 4.0 g (11.6 mmol) of Cbz—L—arginine hydrochloride in a capped glass vial was added 80 ml of cold dry dimethylformamide/pyridine (1:1.v/v) and the contents was stirred at 4° C. until solution was complete. To this was added 2.0 g (10.4 mmol) of 1-(3-dimethylaminopropyl)-3-ethylcarbodi-imide. After 5 min of stirring at 4° C., 150 mg (0.41 mmol) of Rhodamine 110, dissolved in 1.5 ml of dimethylformamide/pyridine (1:1, v/v) was added. Stirring was continued for 2 hr at 4° C. and then for 2 days at room temperature. During this time the reaction solution turned from deep orange to colourless. The reaction solution was transferred to a 250 ml Nalgene centrifuge bottle and concentrated by precipitation with 150 ml of diethyl ether followed by centrifugation at 10,000×g for 20 min. The residue was then dissolved in 10 ml of dimethylformamide, precipitated by the addition of 200 ml of acetone and centrifuged at 10,000×g for 20 min. To the resulting gel, dissolved in 10 ml of dimethylformamide, was added 100 ml of 1.2M HCl, and the solution was centrifuged at 10,000×g for 20 min. The residue was redissolved in 10 ml of dimethylformamide, and the precipitation with 1.2M HCl repeated. The orange-red gel that resulted was next dissolved in 10 ml of methanol and precipitated by the addition of 200 ml of ethyl acetate. After two additional cycles of solution in methanol and reprecipitation with ethyl acetate, the product was dried in an evacuated desiccator at room temperature to yield 340 mg (83%) of a pale pink powder. The solid exhibited no distinct melting point, with gradual evolution of gas above 170° C. (evacuated sealed capillary). The product was judged to be pure by analytical t.l.c., which revealed a single dark spot under u.v. light.

Bis(N—Cbz—argininamido)Rhodamine structually, has the following formula:

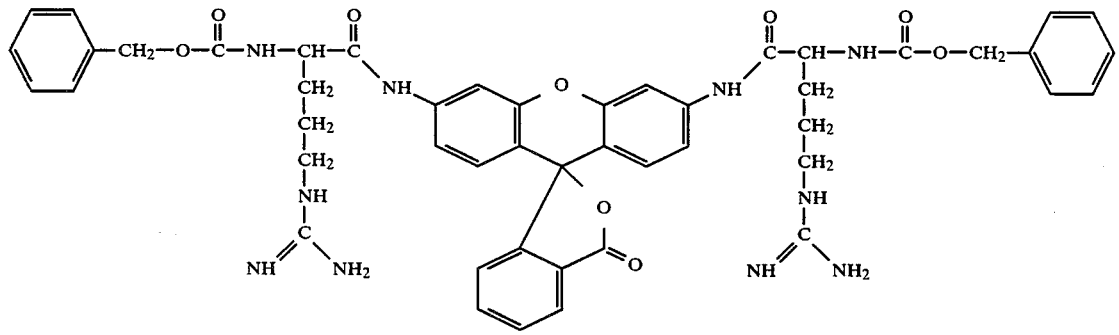

EXAMPLE II

SYNTHESIS OF (Arg—NH)$_2$-RHODAMINE (Cbz—Arg—NH)$_2$-Rhodamine (0.4 g, 0.40 mmole) was deprotected by treatment with 10 ml of 4M-HBr/HOAc for 1 hr at room temperature. The product was precipitated from the reaction solution with 100 ml of ethyl ether and centrifuged at 10,000×g for 20 min. This was followed by three cycles of suspension in ethyl ether and centrifugation at 10,000×g for 20 min. The product was dried over anhydrous calcium sulfate in an evacuated dessciator at room temperature and yielded 0.36 g (90%) of an orange powder. The product was judged to be pure by analytical t.l.c., which revealed a single dark spot under UV.

EXAMPLE III

SYNTHESIS OF DIPEPTIDE DERIVATIVES OF RHODAMINE

The same procedure was used for the synthesis and purification of all the dipeptide Rhodamine substrates, except for that which contained Cbz—Gln in the P$_2$ position.

To 1.22 mmole of Cbz-blocked amino acid in a capped glass vial was added 9 ml of cold, dry DMF/pyridine (1:1, v/v) and the contents were stirred at 4° C. until solution was complete. To this was added 0.215 g (1.12 mmole) of 1-(3-dimethylaminopropyl)-3-ethylcarbodi-imide. After 5 min. of stirring at 4° C., 0.05 g (0.051 mmole) of (Arg—NH)$_2$-Rhodamine, dissolved in 1 ml of DMF/pyridine (1:1, v/v) was added. Stirring was continued at 4° C. for 2 hr and then at room temperature for two days. For the substrate that contained Cbz—Gln in the P$_2$ position the corresponding activated p-nitrophenyl ester (1.22 mmole) was allowed to react with (Arg—NH)$_2$-Rhodamine (0.051 mmole) in DMF/pyridine (1:1, v/v) for ten days at room temperature. All reaction solutions were then concentrated by precipitation, using 10 volumes of ethyl acetate to 1 volume of reaction solution, followed by centrifugation at 10,000×g for 20 min. To the resulting residue dissolved in 1 ml of DMF, was added 10 ml of 1.2M-HCl and the solution then centrifuged at 10,000×g for 20 min. The residue was dissolved in 1 ml of DMF, precipitated by the addition of 10 ml of ethyl acetate, and centrifuged at 10,000×g for 20 min. Additional cycles of solution in 1 ml of DMF, precipitation with 10 ml of ethyl acetate and centrifugation at 10,000×g for 20 min. were repeated until flocculent, pale orange or pink precipitates were obtained (usually after 2–4 cycles). The products, after being dried over anhydrous calcium sulfate either in an evacuated dessicator at room temperature or an evacuated drying pistol at 78° C., appeared as pale orange or pink powders. Yields ranged from 45% to 85%. The products were judged to be pure by analytical t.l.c., which revealed single dark spots under UV.

Other, larger peptide derivatives of Rhodamine are also synthesized in accordance with my three-step process. For example, if one wished to synthesize a tripeptide derivative of Rhodamine, a blocked dipeptide would be substituted in place of the blocked amino acid used in step 3. An example of such a synthesis (for a tripeptide) can be found in Example IV.

EXAMPLE IV

SYNTHESIS OF (Cbz—Ile—Pro—Arg—NH)$_2$-RHODAMINE

To 2.25 g (6.2 mmole) N—Cbz—L—isoleucyl-L-proline in a capped glass vial was added 16 ml cold, dry DMF/pyridine, 1/1, and the contents stirred at 4° C. until solution was complete. To this was added 1.29 g (6.7 mmole) 1-ethyl-3-(3-dimethylaminopropyl)carbodiimide HCl. After 4 min. of stirring at 4° C., 0.30 g (0.31 mmole) of (Arg—NH)$_2$-Rhodamine, dissolved in 4 ml dry DMF/pyridine, 1/1, was added. Stirring was continued at 4° C. for 2 hr and then at room temperature for two days. The reaction mixture was transferred to a 240 ml Nalgene centrifuge bottle and concentrated by precipitation with 100 ml ethyl acetate followed by centrifugation at 10,000×g for 20 min. The residue was then dissolved in 1 ml DMF, and 10 ml 1.2N HCl was added. The precipitate was collected by centrifugation at 10 ml ethyl acetate and centrifuged at 10,000×g for 20 min. After 3 cycles of solution in DMF and reprecipitation with ethyl acetate, the product was dried in an evacuated dessicator at room temperature to yield 180 mg (38.6%) of a pale, pink powder. The product was judged to be pure by analytical thin layer chromatography in a solvent of 2-butanone/acetone/H$_2$O, 8/1/1, which revealed a single, dark spot under U.V. light (R$_f$=0.19).

The bis-substituted peptide derivatives ([Cbz—Ag—NH]$_2$Rhodamine) of Rhodamine can be converted from its non-fluorescent form in which the Rhodamine molecule (the fuorophore core moiety) is in the lactone state, into an intensely fluorescent monosubstituted form in which the fluorophore core moiety is in a quinone state by enzymatic cleavage of a single amide bond. This conversion, which is accompanied with a 3500-fold increase in fluorescence intensity forms the basis for enzyme assays utilizing these bis amide derivatives of Rhodamine can be structurally depicted as:

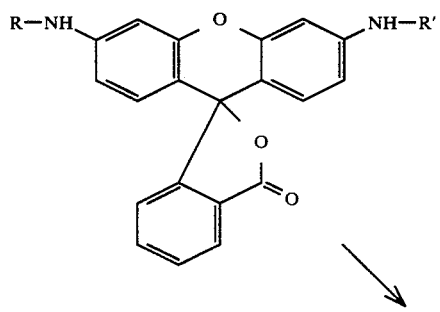

-continued

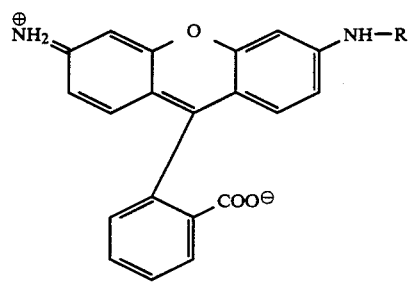

In the above structural formulae, R and R$^1$ (which may be the same substitution or different) are amino acids, amino acid derivatives (blocked or unblocked), or peptide with blocked or unblocked amino acids; that is, R may be the same as R$^1$ and may be a single amino acid such as —Arginine, a peptide such as —Arginine—Proline, —Arginine—Isoleucine, —Arginine—Proline—Isoleucine, —Arginine—Proline—Leucine, or a blocked amino acid as -Arginine-benzyloxycarbonyl. The selectivity of the enzyme assay can be modified by choice of the specific amino acids used, and increasing the size of the amino acid chain to more clearly fit the stereochemical properties of the enzyme. Accordingly, chain having lengths of one to six amino acid residues are preferred in the assays performed to data, however, as more is learned about the specific enzymes desired to be assayed, longer lengths may be preferred to achieve more of an "enzymatic-fit" between the enzyme and the Rhodamine derivative substrate.

When R is not equivalent to R$^1$, other properties than the fluorescence phenomena of the present invention are imparted. For example, R may be a tripeptide, that is a polyamino chain three amino acids in length, designed for a specific enzyme-fit, and R$^1$ can be an octanoyl, that is an alkyl of eight carbons in length. This class of compounds, because of the property of the octanoyl moiety, is lipophilic, and therefore may be used for in situ assays of proteolytic activity of cells in tissue culture and tissue samples. When cells are incubated with such lipophilic compounds, the octanoyl moiety of the compound will become attached to the lipoid membrane of the cell, and the tripeptide moiety portion of the compound will remain on the exterior of the cell, firmly attached by way of the Rhodamine-octanoyl-membrane connection. If the cell to which the compound is attached secretes the necessary enzyme to cleave the peptide-Rhodamine bond, the cleavage of the bond will result in a dramatic increase in the fluorescence of the cell as a result of the remaining membrane-octanoyl-Rhodamine compound firmly attached to the cell. This fluorescence can then be identified by fluorescence microscopy. Although the octanoyl group is mentioned as having this lipophilic property, by no means is this the only lipophilic group that may be substituted (this is merely an example of a specific lipophilic group, other lipophilic groups may also be used to bind the substrate to the cell membrane). The synthesis of one specific lipophilic compound, the octanoyl-substituted compound is set forth in the following Example V.

EXAMPLE V

GENERAL SYNTHESIS OF LIPOPHILIC DERIVATIVES

At room temperature, to 7.12 mg of Cbz—Arg—N-H—Rhodamine dissolved in 1.5 ml of dimethylformamide/pyridine solvent (1/1), was added 30 microliters of octanoyl chloride in three equal aliquots of 10 microliters each at 0, 1, and 2 hrs. After stirring overnight, the resultant product was precipitated with 20 ml of ethyl ether, and collected by centrifugation. After resolution in DMF (dimethylformamide), the precipitation, centrifugation, and resolution steps were repeated twice more. The product of this addition was then deblocked in accordance with the procedure set forth previously.

Addition of the peptide chain (specifically Cbz—Gly—Gly) occurs by first dissolving 36.6 mg of Cbz—Gly—Gly—OH in 3 ml DMF/pyridine solvent (1/1), and adding 19 mg of 1-(3-dimethyl-amino-propyl)-3-ethylcarbodi-imide at 4 degrees centrigrade. After 5 minutes, 4.2 mg of the deblocked derivative dissolved in 1.0 ml of DMF/pyridine solvent (1/1) was added, and the reaction allowed to continue overnight. The product was purified as described for the purification of dipeptide derivatives in Example I.

Structural, the compound made in accordance with this specific Example, is the compound according to the general formula wherein R is $Ch_3(CH_2)_6$—CO—, and $R_2$ is Cbz—Gly—Gly—Arg.

Similarly, the mono(amino)derivatized-Rhodamine, where R is as defined previously, may also carry a protein moiety ($R^1$) such as collagen, specific antibody molecules, etc. In the embodiment, $R^1$ could be, for example, an antibody to a cell surface antigen, and R could be a pharmaceutically active agent. In this manner the blocked fluorogenic compound may be attached to the cell by an antigen-antibody interaction, the pharmaceutically active agent enzymatically cleaved, and the cleavage noted by an increase in fluorescence of the of the cell surface. For example, the addition of collagen to the blocked intermediate Cbz—Gly—Gly—Arg—NH—Rhodamine takes place as described in Example VI.

EXAMPLE VI

SYNTHESIS OF FLUOROGENIC SUBSTRATE ATTACHED TO COLLAGEN

To 5 mg/ml of collagen in water, was added 1-(3-dimethyl-amino-propyl)-3-ethyl-carbodi-imide to 0.1M, and the pH of the resulting solution was adjusted to 5.0. After 3 hours, 1 ml of a water solution containing 1 mg of the blocked compound, Cbz—Gly—Gly—Arg—N-H—Rhodamine, was added, and the reaction was allowed to proceed overnight at 4 degrees centrigrade. The substrate-collagen product was obtained and purified from the reactants by dialysis against water for two days.

By comparison of the kinetic parameters of the bis(N-Cbz-Arginiamido)Rhodamine with several serine proteases to the commonly used coumarin analog, 7-(N-Cbz-L-argininamido)-4-methylcoumarin, the cleavage of the bis(derivatized)Rhodamine to the mono(-derivatized)Rhodamine was found to be accompanied by a large increase in the degree of conjugation of the leaving group relative to that in the substrate, which results in the enhancement of the reactivity of the susceptible amide bond in the substrate. Although it might be expected on the basis of spectral properties alone to obtain an increase in sensitivity of about 10-fold by substituting the Rhodamine derivative for 7-amino-4-methyl-coumarin as the fluorophoric leaving group. A comparison of the sensitivities of (Cbz—Arg—NH)$_2$-Rhodamine and 7(N-Cbz-L-Argininamido)-4methyl-coumarin as substrates for bovine trypsin, human and dog plasmin, and human thrombin revealed (Cbz—Arg—NH)—$_2$Rhodamine to be the better substrate by factors ranging from 50- to 300-fold. The greater sensitivity of the Rhodamine-based substrate arises not only from the fluorophoric leaving group being highly detectable, Cbz—Arg—NH—Rhodamine being 4- to 5-fold more fluorescent than 7-amino-4-methylcoumarin, but also from the reactive-site bonds in (Cbz—Arg—NH)$_2$—Rhodamine being more reactive than that in the coumarin substrate.

A molar fluorescence coefficient, FU/M, whose dimensions are relative fluorescence units per molar concentration of fluorophore, can be used to compare the relative detectabilities of different fluorophores under enzyme assay conditions. Normally in an enzyme assay, the detectability of the fluorophore is optimized by using as the excitation wavelength the absorbance maximum and as the emission wavelength the emission maximum. However, with substrates whose spectral properties are similar to those of their hydrolysis products (such as derivatives of 7-amino-4-methylcoumarin), less than optimal detectability conditions must be used to maximize the spectral differences between the substrate and the product following cleavage. The molar fluorescence coefficients of Rhodamine, Cbz—Arg—NH—Rhodamine, (Cbz—Arg—NH)$_2$Rhodamine, and 7-amino-4-methylcoumarin, obtained from their fluorescence curves are listed in Table 1; the molar fluorescence coefficient for Cbz—Arg—NH—Rhodamine is about 4.5 fold greater than for 7-amino-4-methylcoumarin.

TABLE 1

Molar-fluorescence coefficients for Rhodamine, Cbz—Arg—NH—Rhodamine, 7-amino-4-methylcoumarin and (Cbz—Arg—NH)—Rhodamine at assay wavelengths

| Compound | Value (FU/M) | Relative to that of Rhodamine |
|---|---|---|
| Rhodamine | $1.90 \times 10^{11}$ | 1 |
| Cbz—Arg—NH—Rhodamine | $1.81 \times 10^{10}$ | 0.095 |
| 7-Amino-4-methylcoumarin | $4.15 \times 10^{9}$ | 0.022 |
| (Cbz—Arg—NH)$_2$—Rhodamine | $5.20 \times 10^{6}$ | $2.74 \times 10^{-5}$ |

Molar fluorescence coefficients were measured in 10mM-Hepes buffer, pH 7:5, containing 15% (v/v) ethanol.
Abbreviation:
FU/M, relative fluorescence units per molar concentration of solute.

The enzyme assays that are reported in the present invention disclosure was performed at 22° C. in 10mM-Hepes buffer, pH 7.5, containing 10% (v/v) dimethyl-sulfoxide. For bovine trypsin, 0.02M-CaCl$_2$ was also present. Stock solutions of 0.01M in substrate were prepared in DMF and diluted 33- to 100-fold with buffer prior to assay. The highest substrate concentration, containing from 1% to 3% DMF, was then serially diluted with buffer to obtain a range of substrate concentrations. Enzyme stock solutions were diluted from $10^2$-to $10^5$-fold into buffer immediately prior to being assayed. For all assays, an enzyme concentration was chosen so that less than 5% of the substrate was hydrolyzed. Unless otherwise indicated, 0.01 ml of enzyme was mixed with 0.04 ml of substrate in the bottom of a disposable plastic cuvette. After 5 min., 0.95 ml of 10mM-Hepes buffer, pH 7.5 containing 15% (v/v) ethanol was added, and the fluorescence was immediately recorded using a fluorescence spectrophotometer. The excitation and emission wavelengths were 492 mn, and 523 nm, respectively, both set with a bandwidth of 4 nm. The fluorescence spectrophotometers were standardized using a polymethacrylate embedded with Rhodamine B to ensure that the relative fluorescence was comparable in different experiments.

No spontaneous hydrolysis of the test substrates were observed during the assay procedures.

The kinetic constants $k_{cat}$, $K_m$, and $k_{cat}/K_m$ for the hydrolysis of bis(Arg)Rhodamine, bis(Cbz—Arg)-Rhodamine, and ten Rhodamine-based dipeptide substrates by bovine trypsin, human plasmin, and human thrombin are reported in Tables 2,3, and 4. With each of the substrates, the kinetics of hydrolysis as a function of substrate concentration conformed to that predicted by the Michaelis-Menten rate equation. An important kinetic parameter is the specificity constant, $k_{cat}/K_m$, since this constant is probably the most useful parameter for comparing the reactivity of different substrates with the same or different enzymes.

The Rhodamine-based amino acid and dipeptide substrates exhibited a broad range of specificity constants. Whereas bis(Arg)Rhodamine was a poor substrate for bovine trypsin and was not hydolyzed at all by human plasmin and by human thrombin, addition of Cbz-blocking groups to this substrate greatly increased the $k_{cat}/K_m$ values with each of these enzymes, greater than 400-fold with bovine trypsin. Further extension of the substrate with certain Cbz-blocked amino acids in the $P_2$ position resulted in additional increases in $k_{cat}/K_m$ values. The highest degree of specificity with the dipeptide substrates was observed with bovine trypsin reported in Table 2. The range in $k_{cat}$ values was 16-fold, in $K_m$ values 4-fold and in $k_{cat}/K_m$ values 7-fold. The most preferred amino acid in the $P_2$ position was Gly and the least preferred was Leu.

TABLE 2

Kinetic Constants for the Hydrolysis of Amino Acid and Dipeptide Substrates by Bovine Trypsin.

| Substrate | $k_{cat}$ (sec$^{-1}$) | $K_m$ ($\mu$M) | $k_{cat}/K_m$ (M$^{-1}$sec$^{-1}$) |
|---|---|---|---|
| Bis(Arg)rhodamine | — | — | 454 |
| Bis(Z—Arg)rhodamine | 23.9 | 139 | 172,000 |
| Bis(Z—Ala—Arg)rhodamine | 66.3 | 42.4 | 1,560,000 |
| Bis(Z—Gln—Arg)rhodamine | 44.1 | 73.7 | 598,000 |
| Bis(Z—Glu—Arg)rhodamine | 51.9 | 110 | 472,000 |
| Bis(Z—Gly—Arg)rhodamine | 108 | 64.7 | 1,670,000 |
| Bis(Z—Leu—Arg)rhodamine | 25.0 | 101 | 248,000 |
| Bis(Z—Met—Arg)rhodamine | 25.6 | 100 | 256,000 |
| Bis(Z—Phe—Arg)rhodamine | 43.2 | 57.2 | 755,000 |
| Bis(Z—Pro—Arg)rhodamine | 62.2 | 61.6 | 1,010,000 |
| Bis(Z—Trp—Arg)rhodamine | 6.92 | 27.2 | 254,000 |
| Bis(Z—Val—Arg)rhodamine | 21.4 | 31.3 | 684,000 |

Z = Cbz

With human plasmin, reported in Table 3, a lesser degree of specificity was observed with the dipeptide substrates as compared with bovine trypsin, (reported in Table 2). The range in $k_{cat}$ values was about 33-fold, in $K_m$ values about 5-fold and in $k_{cat}/K_m$ values about 12-fold. The most preferred amino acid in the $P_2$ position was Phe and the least preferred was Glu.

TABLE 3

Kinetic Constants for the Hydrolysis of Amino Acid and Dipeptide Substrates by Human Plasmin.

| Substrate | $k_{cat}$ (sec$^{-1}$) | $K_m$ ($\mu$M) | $k_{cat}/K_m$ (M$^{-1}$sec$^{-1}$) |
|---|---|---|---|
| Bis(Arg)rhodamine | No Hydrolysis | | |
| Bis(Z—Arg)rhodamine | 0.075 | 62.4 | 1,200 |
| Bis(Z—Ala—Arg)rhodamine | 1.12 | 138 | 8,120 |
| Bis(Z—Gln—Arg)rhodamine | 0.80 | 120 | 6,700 |
| Bis(Z—Glu—Arg)rhodamine | 0.27 | 97.4 | 2,800 |
| Bis(Z—Gly—Arg)rhodamine | 0.40 | 61.5 | 6,500 |
| Bis(Z—Leu—Arg)rhodamine | 0.39 | 61.8 | 6,300 |
| Bis(Z—Met—Arg)rhodamine | 0.50 | 91.1 | 5,500 |
| Bis(Z—Phe—Arg)rhodamine | 8.92 | 294 | 30,300 |
| Bis(Z—Pro—Arg)rhodamine | 0.79 | 89.7 | 8,800 |
| Bis(Z—Trp—Arg)rhodamine | 3.44 | 128 | 26,900 |
| Bis(Z—Val—Arg)rhodamine | 1.14 | 76.4 | 14,900 |

Z = Cbz

The greatest range in specificity constants with the dipeptide substrates was observed with human thrombin, reported in Table 4. No hydrolysis could be detected with Phe or Trp in the $P_2$ position, whereas the dipeptide substrate with Pro in the $P_2$ position exhibited a $k_{cat}/K_m$ value of 368,000M$^{-1}$sec$^{-1}$. For those dipeptide substrates that were hydrolyzed, the range in $k_{cat}$ values was 68-fold, in $K_m$ values 7-fold and in $k_{cat}/K_m$ values 165-fold.

TABLE 4

Kinetic Constants for the Hydrolysis of Amino Acid and Dipeptide Substrates by Human Thrombin.

| Substrate | $k_{cat}$ (sec$^{-1}$) | $K_m$ ($\mu$M) | $k_{cat}/k_m$ (M$^{-1}$sec$^{-1}$) |
|---|---|---|---|
| Bis(Arg)rhodamine | No Hydrolysis | | |
| Bis(Z—Arg)rhodamine | 0.072 | 16.4 | 4,400 |
| Bis(Z—Ala—Arg)rhodamine | 0.32 | 21.6 | 15,000 |
| Bis(Z—Gln—Arg)rhodamine | 0.15 | 64.4 | 2,330 |
| Bis(Z—Glu—Arg)rhodamine | 1.46 | 36.6 | 39,900 |
| Bis(Z—Gly—Arg)rhodamine | 0.16 | 22.8 | 7,000 |
| Bis(Z—Leu—Arg)rhodamine | 0.14 | 23.8 | 5,900 |
| Bis(Z—Met—Arg)rhodamine | 0.053 | 24.2 | 2,200 |
| Bis(Z—Phe—Arg)rhodamine | No Hydrolysis | | |
| Bis(Z—Pro—Arg)rhodamine | 3.42 | 9.30 | 368,000 |
| Bis(Z—Trp—Arg)rhodamine | No Hydrolysis | | |
| Bis(Z—Val—Arg)rhodamine | 0.60 | 25.8 | 23,000 |

Z = Cbz

The kinetic parameters for the hydrolysis of bis(Cbz—Arg)Rhodamine, bis(Cbz—Gly—Arg)Rhodamine, bis(Cbz—Phe—Arg)Rhodamine, and bis(Cbz—Pro—Arg)Rhodamine by bovine trypsin, human plasmin, and human thrombin are listed in Table 5. This data illustrates the large increase in specificity that is effected by the addition of an appropriate amino acid in the $P_2$ position. For example, with human thrombin the specificity constant for bis(Cbz—Pro—Arg)Rhodamine is 83-fold larger than for bis(A—Arg)Rhodamine. In general, the large increase in $k_{cat}/K_m$ that results from extending bis(R—Arg)Rhodamine by a single amino acid appears to reflect an increase in $k_{cat}$ as opposed to a decrease in $K_m$. Table 5 also illustrates certain of the substrates are selective, i.e., efficiently hydrolyzed by one enzyme and not by others. Each of the enzymes most preferred a different amino acid in the $P_2$ position. The most specific substrate for human, plasmin, bis(Cbz—Phe—Arg)Rhodamine, is not hydrolyzed by human thrombin, and the most specific substrate for human thrombin, bis(Cbz—Pro—Arg)Rhodamine, is one of the least specific substrates for human plasmin.

As stated previously, this specificity can be increased even further by utilizing a tripeptide prepared in accordance with Example 4 in lieu of the dipeptide listed in Table 5.

TABLE 5

Kinetic Constants for the Hydrolysis of Bis (Z—Arg) Rhodamine and the Most Preferred Dipeptide Substrates for Bovine Trypsin, Human Plasmin and Human Thrombin. The kinetic constants of the most preferred substrate for each enzyme are enclosed in a rectangle.

| Substrate | Kinetic Constants[a] | Bovine Trypsin | Human Plasmin | Human Thrombin |
|---|---|---|---|---|
| Bis(Z—Arg)rhodamine | $k_{cat}$ | 23.9 | 0.075 | 0.072 |
| | $K_m$ | 139 | 62.4 | 16.4 |
| | $k_{cat}/K_m$ | 172,000 | 1,200 | 4,400 |
| Bis(Z—Gly—Arg)rhodamine | $k_{cat}$ | 108 | | |
| | $K_m$ | 64.7 | | |
| | $k_{cat}/K_m$ | 1,670,000 | | |
| Bis(Z—Phe—Arg)rhodamine | $k_{cat}$ | | 8.92 | No Hydrolysis |
| | $K_m$ | | 294 | |
| | $k_{cat}/K_m$ | | 30,300 | |
| Bis(Z—Pro—Arg)rhodamine | $k_{cat}$ | | 0.79 | 3.42 |
| | $K_m$ | | 89.7 | 9.30 |
| | $k_{cat}/K_m$ | | 8,800 | 368,000 |

In summary, the present invention discloses the synthesis of a series of dipeptide Rhodamine-based compounds and to assess their uses as fluorogenic substrates for proteases in terms of sensitivity, specificity and selectivity. The Rhodamine-based amino acid and dipeptide substrates of the present invention are extremely sensitive when tested upon the reactivity of the reactive-site bond and on the detectability of the leaving group as a hydrolysis product; the reactive-site bond in (Cbz—Arg—NH)₂—Rhodamine is more reactive than that in 7-(N-Cbz-L-argininamido)-4-methylcoumarin, and the hydrolysis product, Cbz—Arg—NH—Rhodamine, is more detectable than 7-amino-4-methylcoumarin. Analysis of the spectral properties of Cbz—Phe—Arg—NH—Rhodamine and Cbz—Pro—Arg—NH—Rhodamine, show them to be identical to those of Cbz—Arg—NH—Rhodamine, thus indicating that neither the length of the peptide chain nor its amino acid composition influences the spectral properties of the hydrolysis products, at least for those Rhodamine-based substrates with an Arg in the P₁ position.

The specificity of a substrate for any enzyme can be described by the specificity contant, $k_{cat}K/m$, which reflects the efficiency with which the enzyme catalyzes the hydrolysis of the substrate. The Rhodamine-based substrates, from the unblocked, single amino acid substrate (Arg—NH)₂—Rhodamine to the blocked, dipeptide and higher substrates, exhibited a wide range of specificity contants: (Arg=NH)₂—Rhodamine was not hydrolyzed by human or dog plasmin or human thrombin; addition of Cbz blocking groups to yield (Cbz—Arg—NH)₂—Rhodamine resulted in significant hydrolysis by these proteinases. Further extension with certain blocked amino acids in the P₂ position resulted in an even larger increase in the specificity constant. Comparison of the kinetic constants for the best dipeptide substrates with those for (Cbz—Arg—NH)₂—Rhodamine indicated that the large increase in $k_{cat}/K_m$ afforded by extending the single amino acid substrate with an appropriate P₂ residue was primarily the result of a very large increase in $k_{cat}$ as opposed to a decrease in $K_m$. This large increase in $k_{cat}$ suggests the orientation (enzyme-fit) of the dipeptide substrate in the proteinase's active site allowed for more efficient catalysis compared to the single amino acid substrate.

The specificity exhibited by many proteinases depends to a large extent upon the the interaction of subsite amino acids in the proteinase's active site with extended amino acid residues in the peptide substrate. This can be characterized, with synthetic substrates, by observing variations in the specificity constant upon substituting or altering a single residue in the peptide substrate. Since plasmin and thrombin are trypsin-like serine proteinases and, as such, prefer Arg or Lys in the P₁ position, the specificity constants with (Cbz—Arg—NH)₂—Rhodamine were expected to be similar. However, with the substrates in the dipeptide series, each with an ARg in the P₁ position and a different Cbz-blocked amino acid in the P₂ position, these two proteinases exhibited distinct preferences for the amino acid in the P₂ position. Whereas human plasmin most preferred Phe in the P₂ position, human thrombin by far preferred Pro in the P₂ position. Furthermore, human thrombin did not hydrolyze those substrates with Phe or Trp in the P₂ position.

The selectively of a substrate refers to whether it is efficiently hydrolyzed by one enzyme and not by others. With the large range of specificity constants exhibited by the substrates in the dipeptide series, the possibility arose that certain of the dipeptide substrates may be selective. A comparison of the $k_{cat}/K_m$ values indicates that some of the best substrates for human plasmin were among the worst substrates for human thrombin, and vice versa. The substrates with the two hightest specificity constants with human plasmin, (Cbz—Phe—Arg—NH)₂—Rhodamine and (Cbz—Trp—Arg—NH)₂—Rhodamine, were not hydrolyzed by human thrombin. Conversely, the best substrate for human thrombin, (Cbz—Pro—Arg—NH)₂—Rhodamine was one of the worst substrates for human plasmin, the difference in $k_{cat}/K_m$ values being 40-fold. This high degree of selectivity, observed with two trypsin-like serine proteinases whose substrate specificities might otherwise have been thought to be similar, was afforded by extending the nonselective substrate (Cbz—Arg—NH)$_2$—Rhodamine by a single amino acid residue.

Thus, while we have illustrated and described the preferred embodiment of my invention; it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview, of the following claims.

Having thus described our invention and the manner and process of making and using it, in such full, clear, concise, and exact terms so as to enable any person skilled in the art to which it pertains, or with which is it most nearly connected, to make and use the same.

We claim:

1. A compound of the formula:

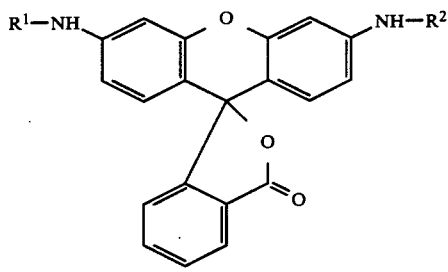

wherein R$^1$ and R$^2$, which are the same or different, are selected from the group consisting of amino acids, amino acid derivatives, blocked amino acids, blocked amino acid derivatives, and peptides.

2. A compound according to claim 1 wherein R$^1$ and R$^2$ are amino acids, blocked amino acids, or peptides.

3. A compound according to claim 1 wherein R$^1$ and R$^2$ are peptides.

4. The compounds according to claim 3 wherein R$^1$ and R$^2$ comprise a peptide in which the amino acid bound to the amino constituent of said formula is arginine.

5. A compound according to claim 1 wherein R$^1$ and R$^2$ are peptides.

6. A compound according to claim 5 wherein R$^1$ and R$^2$ are selected from the group consisting of dipeptides and tripeptides.

7. A compound according to claim 6 wherein at least one of the amino acid residue compounds comprising said dipeptide or tripeptide is arginine.

8. A compound of the formula:

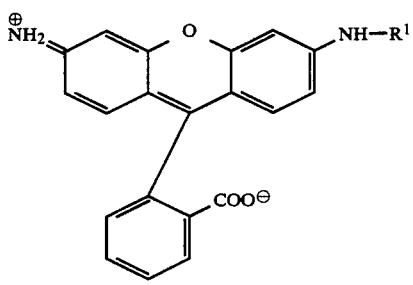

wherein R$^1$ is selected from the group consisting of amino acids, amino acid derivatives, blocked amino acids, blocked amino acid derivatives, and peptides.

9. A compound according to claim 8 wherein R$^1$ is selected from amino acids and peptides.

10. The compound according to claim 9 wherein R$^1$ is a peptide.

* * * * *

UNITED STATES PATENT AND TRADEMARK OFFICE
CERTIFICATE OF CORRECTION

PATENT NO. : 4,557,862
DATED : December 10, 1985
INVENTOR(S) : Walter, F. Mangel, Stephen P. Leytus, L. Lee Melhado It is certified that error appears in the above—identified patent and that said Letters Patent is hereby corrected as shown below:

Column 4, line 6, delete "dessciator", and insert
--dessicator--;

Column 8, line 56, delete "was", and insert --were--.

Signed and Sealed this

First Day of July 1986

[SEAL]

Attest:

Attesting Officer

DONALD J. QUIGG

Commissioner of Patents and Trademarks